(12) United States Patent
Penman et al.

(10) Patent No.: US 11,740,202 B2
(45) Date of Patent: Aug. 29, 2023

(54) POINT-OF-CARE APPARATUS AND METHODS FOR DETECTING CANCER USING ELECTROCHEMICAL IMPEDANCE OR CAPACITANCE SPECTROSCOPY

(71) Applicant: Sapphire Diagnostics, LLC, San Diego, CA (US)

(72) Inventors: Andrew Douglas Penman, Birmingham, AL (US); Marcus Willard Smith, Birmingham, AL (US); Catalina Valencia, San Diego, CA (US); Sergei A Svarovsky, San Diego, CA (US)

(73) Assignee: ADVANCED TEAR DIAGNOSTICS, LLC., Birmingham, AL (US)

( * ) Notice: Subject to any disclaimer, the term of this patent is extended or adjusted under 35 U.S.C. 154(b) by 799 days.

(21) Appl. No.: 16/119,989

(22) Filed: Aug. 31, 2018

(65) Prior Publication Data
US 2019/0072560 A1 Mar. 7, 2019

Related U.S. Application Data

(60) Provisional application No. 62/553,773, filed on Sep. 1, 2017.

(51) Int. Cl.
*G01N 27/327* (2006.01)
*G01N 33/574* (2006.01)
(Continued)

(52) U.S. Cl.
CPC ......... *G01N 27/327* (2013.01); *A61B 5/1486* (2013.01); *A61B 5/14532* (2013.01);
(Continued)

(58) Field of Classification Search
CPC .......... G01N 33/57488; G01N 27/026; G01N 27/02; G01N 27/327; G01N 27/22;
(Continued)

(56) References Cited

U.S. PATENT DOCUMENTS 5,672,256 A * 9/1997 Yee .................... G01N 27/3272
435/817
5,753,519 A 5/1998 Durst et al.
(Continued)

OTHER PUBLICATIONS

Diaconu et al ("Electrochemical immunosensors in breast and ovarian cancer", Clinica Chimica Acta, 425, 2013, 128-138) (Year: 2013).*

(Continued)

*Primary Examiner* — Christopher L Chin
(74) *Attorney, Agent, or Firm* — Procopio, Cory, Hargreaves & Savitch LLP

(57) ABSTRACT

The presence of biomarkers or other analytes can be detected in the bodily fluid using Electrochemical Impedance Spectroscopy (EIS) or Electrochemical Capacitance Spectroscopy (ECS) in devices, such as handheld point-of-care devices. The devices, as well as systems and methods, utilize using Electrochemical Impedance Spectroscopy (EIS) or Electrochemical Capacitance Spectroscopy (EIS) in combination with an antibody or other target-capturing (Continued)

molecule on a working electrode. Imaginary impedance or phase shift, as well as background subtraction, also may be utilized.

9 Claims, 15 Drawing Sheets

(51) Int. Cl.
*A61B 5/1486* (2006.01)
*G01N 33/543* (2006.01)
*A61B 5/145* (2006.01)
*G01N 27/02* (2006.01)
*G01N 27/22* (2006.01)

(52) U.S. Cl.
CPC ............ *G01N 27/02* (2013.01); *G01N 27/026* (2013.01); *G01N 27/22* (2013.01); *G01N 27/3275* (2013.01); *G01N 33/5438* (2013.01); *G01N 33/57415* (2013.01); *G01N 33/57488* (2013.01)

(58) Field of Classification Search
CPC ............ G01N 27/3275; G01N 33/5438; G01N 33/57415; A61B 5/1486; A61B 5/14532; A61B 5/1468; A61B 5/150022; A61B 5/150358

USPC ............ 204/403.01, 403.06, 412; 422/82.01; 435/287.2; 436/806
See application file for complete search history.

(56) References Cited

U.S. PATENT DOCUMENTS 5,945,286 A * 8/1999 Krihak ................. C12Q 1/6825
422/50
2017/0234894 A1 * 8/2017 LaBelle ............... G01N 33/743
435/7.4

OTHER PUBLICATIONS

Hnaien et al. ("Immobilization of specific antibody on SAM functionalized gold electrode for rabies virus detection by electrochemical impedance spectroscopy", Biochemical Engineering Journal, 39, 2008, 443-449) (Year: 2008).*
Office Action for related U.S. Appl. No. 16/121,474 dated Apr. 30, 2021 (15 pages).

* cited by examiner

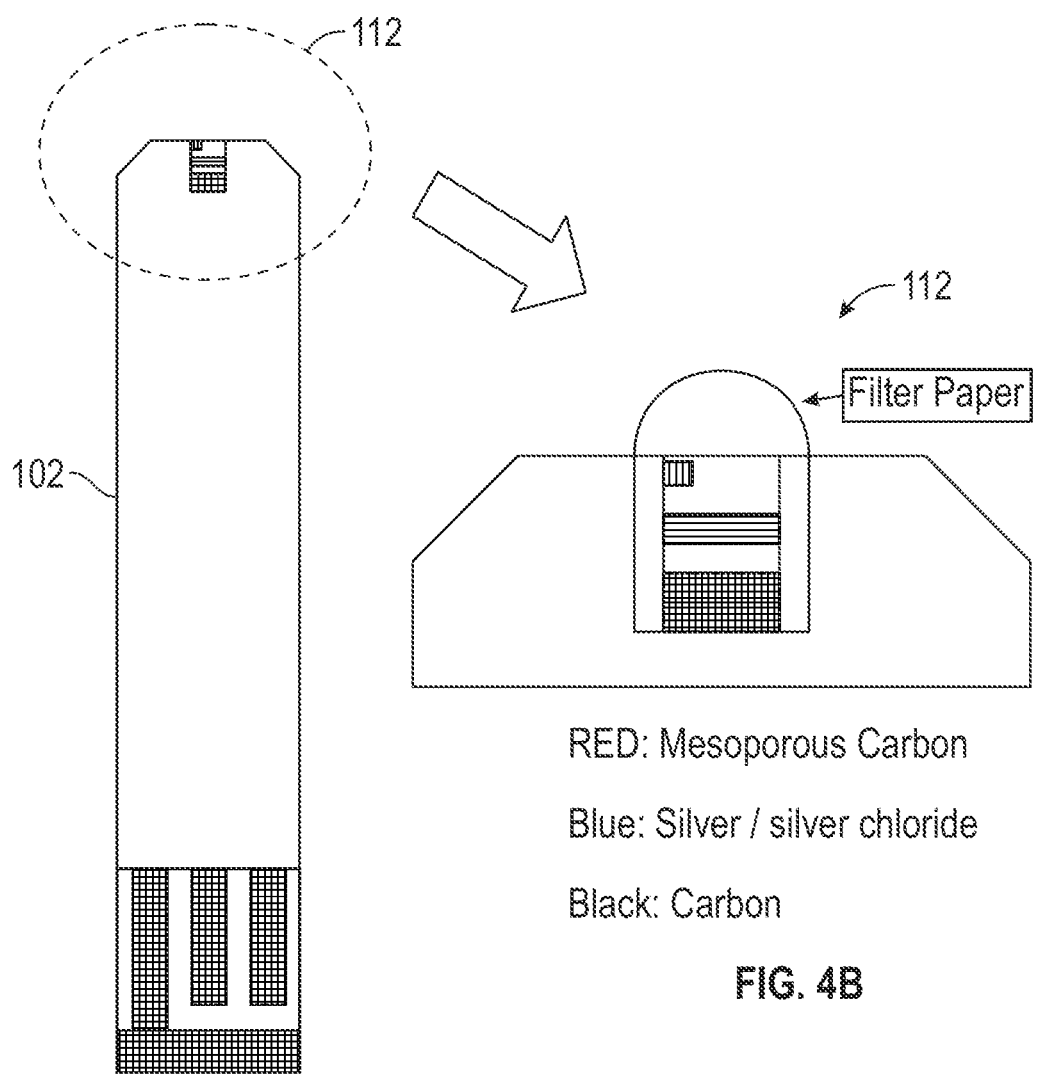

Carbon      Ag/AgCl      Insulayer      Mesoporous Carbon
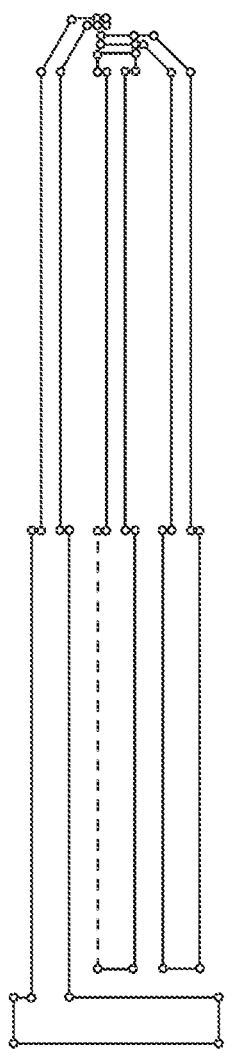
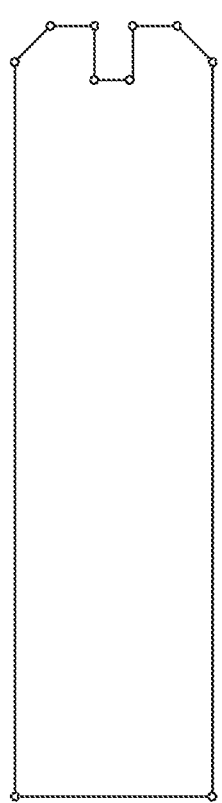
FIG. 5A      FIG. 5B      FIG. 5C      FIG. 5D

|  | Lactoferrin Sensors | | | | | | | Blank Sensors | | | | |
|---|---|---|---|---|---|---|---|---|---|---|---|---|
| Freq (Hz) | e12 | f3 | e10 | Avg | %RSD | %change | Freq (Hz) | f6 | e6 | e5 | Avg | %RSD |
| 97.66 | -3841 | -4618 | -4100 | -4186 | 9% | 14% | 97.66 | -3632 | -3774 | -3591 | -3666 | 3% |
| 81.38 | -4131 | -5033 | -4419 | -4528 | 10% | 19% | 81.38 | -3721 | -3889 | -3760 | -3790 | 2% |
| 69.75 | -4336 | -5339 | -4651 | -4775 | 11% | 25% | 69.75 | -3698 | -3892 | -3828 | -3806 | 3% |
| 57.44 | -4444 | -5517 | -4780 | -4914 | 11% | 32% | 57.44 | -3573 | -3791 | -3794 | -3719 | 3% |
| 46.50 | -4458 | -5569 | -4800 | -4942 | 12% | 39% | 46.50 | -3373 | -3613 | -3677 | -3554 | 5% |
| 37.56 | -4382 | -5495 | -4715 | -4864 | 12% | 46% | 37.56 | -3124 | -3386 | -3497 | -3336 | 6% |
| 31.50 | -4232 | -5301 | -4541 | -4691 | 12% | 52% | 31.50 | -2856 | -3131 | -3279 | -3089 | 7% |
| 25.70 | -4020 | -5020 | -4302 | -4447 | 12% | 57% | 25.70 | -2585 | -2874 | -3046 | -2835 | 8% |
| 21.23 | -3768 | -4684 | -4019 | -4157 | 11% | 61% | 21.23 | -2323 | -2620 | -2813 | -2585 | 10% |
| 17.44 | -3503 | -4318 | -3720 | -3847 | 11% | 63% | 17.44 | -2081 | -2386 | -2592 | -2353 | 11% |
| Min | -4458 | -5569 | -4800 | -4942 | 12% | 30% | Min | -3721 | -3892 | -3828 | -3806 | 2% |
| Peak freq | 46.50 | 46.50 | 46.50 | 46.50 | 0% |  | Peak freq | 81.38 | 69.75 | 69.75 | 69.75 | 10% |

FIG. 7

|  | Lactoferrin Sensors | | | | | | | Blank Sensors | | | | |
|---|---|---|---|---|---|---|---|---|---|---|---|---|
| Freq (Hz) | e12 | f3 | e10 | Avg | %RSD | %change | Freq (Hz) | f6 | e6 | e5 | Avg | %RSD |
| 97.66 | -49.3 | -53.0 | -51.0 | -51.1 | 4% | 21% | 97.66 | -42.6 | -42.3 | -44.5 | -43.1 | 3% |
| 81.38 | -46.4 | -49.9 | -47.8 | -48.0 | 4% | 23% | 81.38 | -39.0 | -38.9 | -41.3 | 39.7 | 3% |
| 69.75 | -43.1 | -46.2 | -44.4 | -44.6 | 3% | 27% | 69.75 | -35.1 | -35.2 | -37.8 | -36.0 | 4% |
| 57.44 | -39.6 | -42.3 | -40.7 | -40.9 | 3% | 29% | 57.44 | -31.3 | -31.6 | -34.2 | 32.4 | 5% |
| 46.50 | -36.0 | -38.3 | -37.0 | -37.1 | 3% | 33% | 46.5 | -27.6 | -28.0 | -30.7 | 28.8 | 6% |
| 37.56 | -32.6 | -34.5 | -33.4 | -33.5 | 3% | 35% | 37.56 | -24.2 | -24.8 | -27.3 | -25.4 | 6% |
| 31.50 | -29.3 | -30.8 | -30.0 | -30.0 | 2% | 37% | 31.5 | -21.2 | -21.9 | -24.3 | -22.5 | 7% |
| 25.70 | -26.2 | -27.4 | -26.7 | -26.8 | 2% | 39% | 25.7 | -18.6 | -19.3 | -21.6 | -19.8 | 8% |
| 21.23 | -23.4 | -24.3 | -23.8 | -23.8 | 2% | 40% | 21.23 | -16.2 | -17.0 | -19.2 | -17.5 | 9% |
| 17.44 | -20.9 | -21.4 | -21.1 | -21.1 | 1% | 40% | 17.44 | -14.2 | -15.1 | -17.1 | -15.5 | 10% |
| Min | -59.9 | -63.5 | -61.4 | -61.6 | 3% | 5% | Min | -59.3 | -58.7 | -57.9 | -58.6 | 1% |
| Peak freq | 371.1 | 371.1 | 371.1 | 371.1 | 0% | 0% | Peak freq | 459.0 | 459.0 | 371.1 | 459.0 | 11% |
|  |  |  |  |  |  |  |  |  |  |  |  |  |
| Lfn | 371.1 | -59.9 | -63.5 | -61.4 | -61.6 | 3% | 5% | 371.1 | -59.1 | -58.4 | -57.9 | -58.5 | 1% |
| Blank | 459.0 | -59.5 | -63.0 | -60.9 | -61.1 | 3% | 4% | 459.0 | -59.3 | 58.7 | -57.8 | -58.6 | 1% |

FIG. 8

Hardware Circuit block Diagram

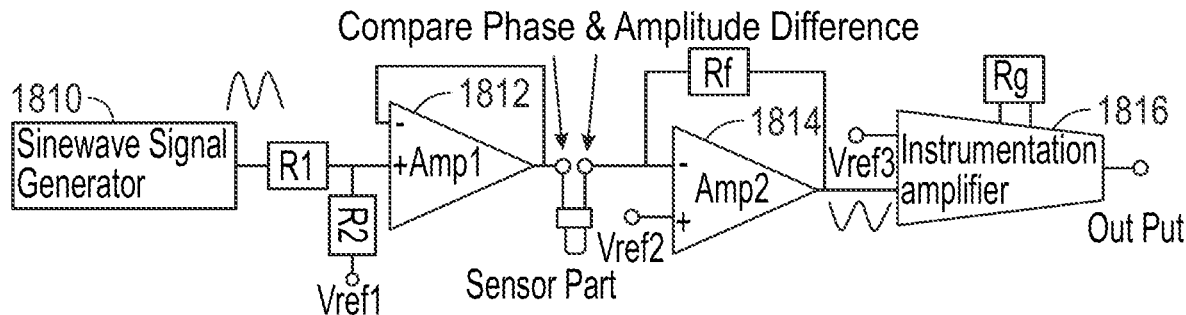

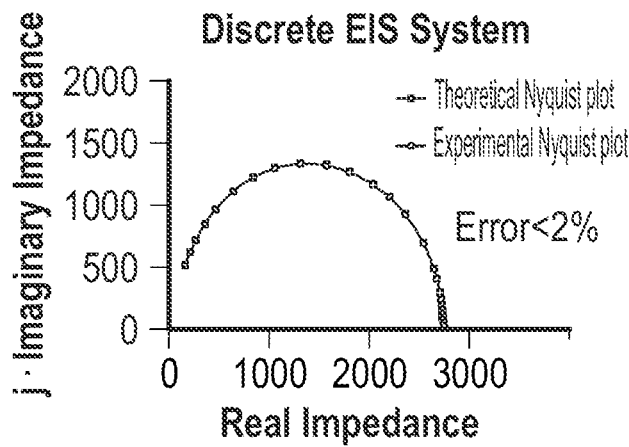

Electrical impedance spectroscopy uses frequency domain techniques to detect specific biomolecules. Frequency domain is useful since only a small perturbation is introduced into the system, thus preserving the integrity of the biologic system. The technique also permits examination of the response of the system over a spectrum of frequencies, greatly increasing the specificity of the detection.

FIG. 11

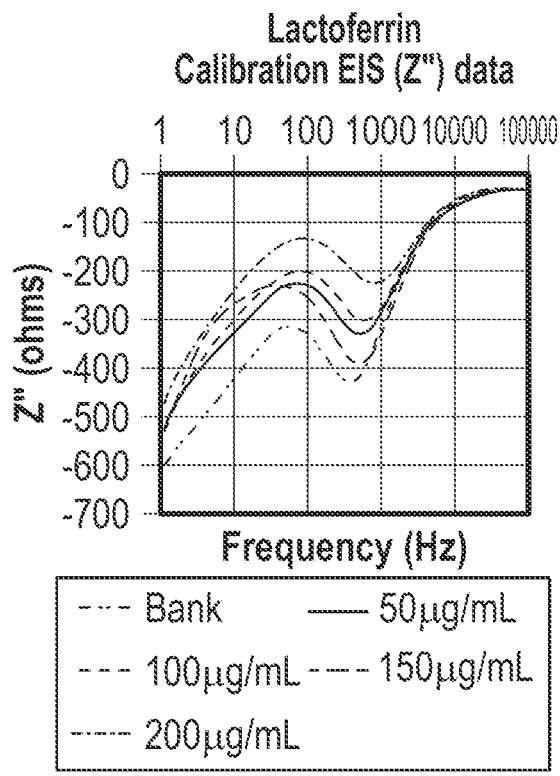

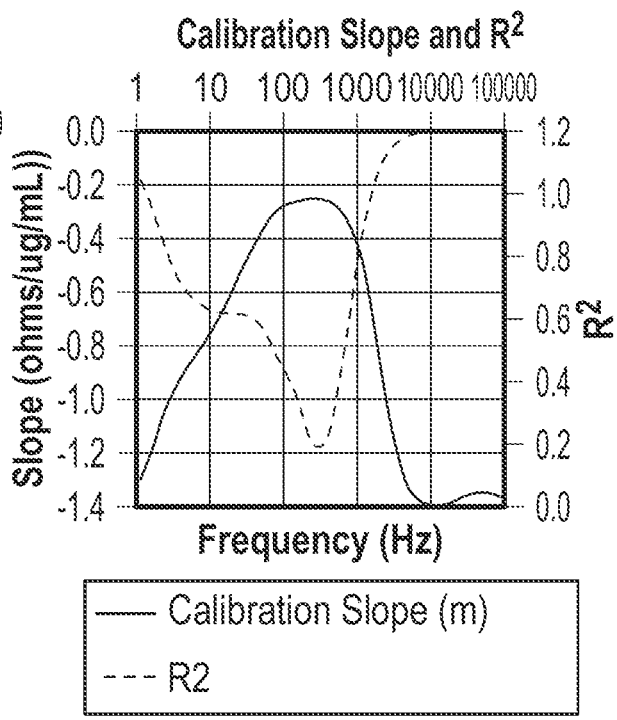

FIG. 12

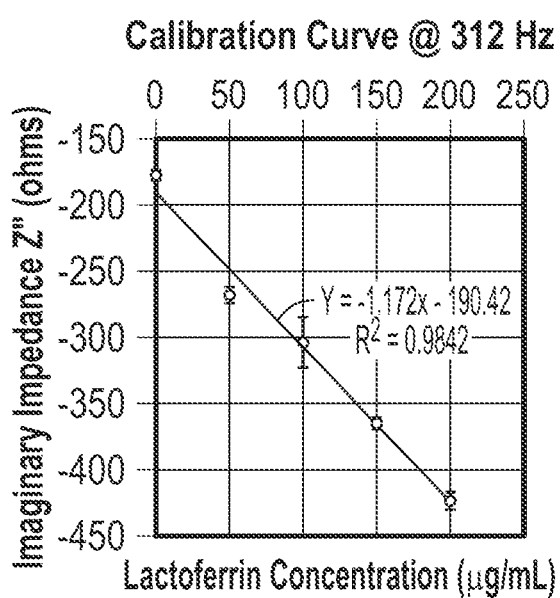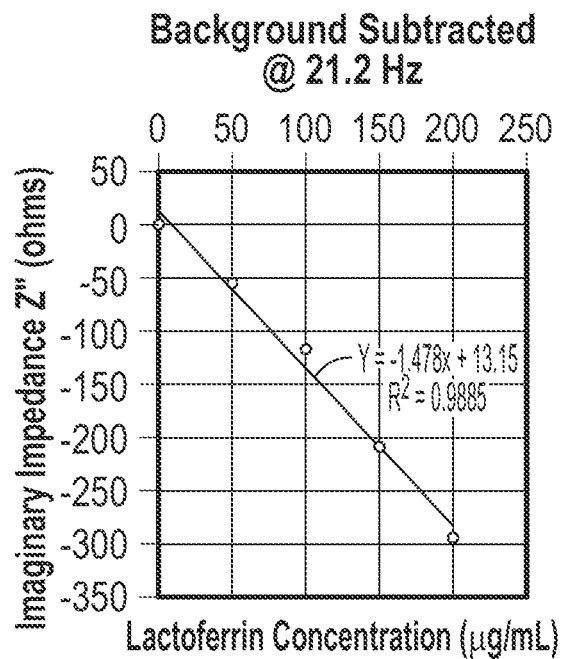
FIG. 13
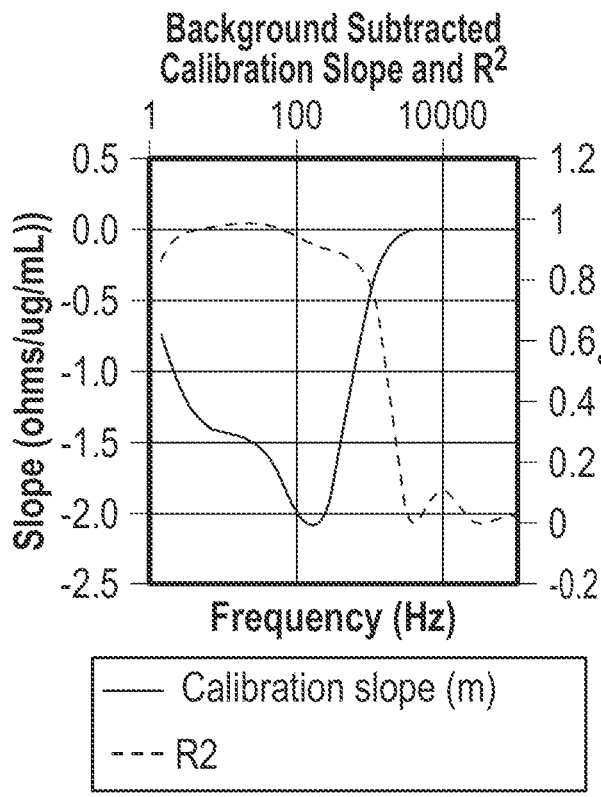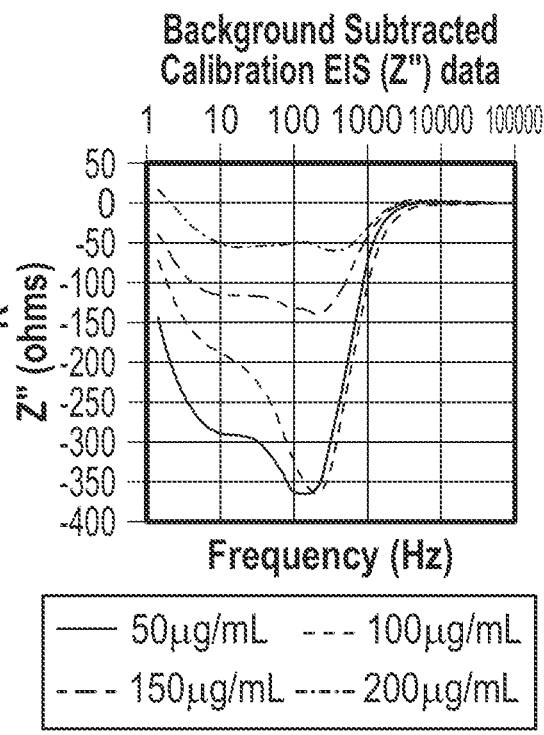
FIG. 14

POINT-OF-CARE APPARATUS AND METHODS FOR DETECTING CANCER USING ELECTROCHEMICAL IMPEDANCE OR CAPACITANCE SPECTROSCOPY

RELATED APPLICATION INFORMATION

This application claims priority under 35 U.S.C. 119(e) to provisional application 62/553,773, entitled "Point-of-Care Apparatus and Methods for Detecting Cancer Using Electrochemical Impedance or Capacitance Spectroscopy", filed Sep. 1, 2017, which is incorporated herein by reference in its entirety.

BACKGROUND

1. Technical Field

This disclosure is related to detection tools, diagnostics and related methods involving the use of an electrochemical sensor in conjunction with electrochemical impedance spectroscopy or electrochemical capacitance spectroscopy, and more particularly to using such tools to detect cancer via biomarkers contained in bodily fluids using such detection tools, diagnostics, and related methods.

2. Related Art

Many different analyte detection devices and systems exist. However, those that can be practically applied in a clinical, point of care or other setting requiring accuracy and reliability are fairly limited and tend to be complex and expensive.

SUMMARY

Embodiments herein relate to apparatus, systems, and methods for analyte detection and diagnosis.

The presence of biomarkers or other analytes can be detected in bodily fluids, such as blood, gingival crevicular fluid, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, and suspect tissues or any other constituents of the body which may contain the target molecule of interest using Electrochemical Impedance Spectroscopy (EIS) or Electrochemical Capacitance Spectroscopy (ECS), in a handheld point-of-care device, as well as in systems and methods that utilize EIS and/or ECS in combination with a molecular recognition element (MRE) (e.g., a synthetic antibody or bio-mimetic polymer, such as a peptoid) or other target-capturing molecule (e.g., a naturally occurring antibody) on the working electrode of an electrochemical sensor. Such MRE's and target-capturing molecules may include without limitation chemical probes, antibodies, enzymes, receptors, ligands, antigens, DNA, RNA, peptides, and oligomers.

In some embodiments, following perturbation of an electrochemical sensor with an alternating current voltage applied at a discrete frequency or across a range of frequencies, complex impedance, real impedance, imaginary impedance and/or phase shift are utilized to measure the presence or concentration of an analyte.

These and other aspects will be described in more detail in the drawings and description that follow.

BRIEF DESCRIPTION OF THE DRAWINGS

FIGS. 4A-B is a diagram illustrating another example sensor strip that can be used in with the device of FIG. 1;

FIGS. 5A-D is a diagram illustrating another example sensor strip that can be used in with the device of FIG. 1A-B;

FIG. 7 is a graph illustrating a subset of data from an imaginary impedance approach to analyte detection through EIS after scanning from 1 to 100,000 Hz at a formal potential of 0.1V and an AC potential of 5 mV;

FIG. 8 is a graph of a subset of data from a phase shift approach to analyte (lactoferrin) detection through EIS;

FIG. 11 is a diagram illustrating an example hardware circuit that can be used in conjunction with the sensors of FIGS. 3-5 and included in the device of FIG. 1A-B;

FIG. 12 depicts EIS data (left) after scanning from 100,000 Hz to 1 Hz at a formal potential of 0.1V and an AC potential of 5 mV over a range of lactoferrin concentrations (0-200 μg/mL). The optimal frequency to prepare a quantitative calibration line was found to be around 312 Hz. A plot of $R^2$ and slope against frequency (right) can be used to pick a single frequency or range of frequencies at which to generate a calibration line.

FIG. 13 shows a comparison of original (left) and background subtracted (right) lactoferrin calibration lines at 312 Hz and 21.2 Hz in the form of y=mx+c with $R^2$ values of 0.9842 and 0.9885 respectively.

FIG. 14 shows a plot of background subtracted $R^2$ and slope against frequency (left) and background subtracted EIS scans from 100,000 Hz to 1 Hz (right) at a formal potential of 0.1V and an AC potential of 5 mV over a range of lactoferrin concentrations (50-200 μg/mL).

DETAILED DESCRIPTION

Embodiments herein relate to apparatus, systems, and methods for analyte detection and diagnosis using Electrochemical Impedance Spectroscopy (EIS) or Electrochemical Capacitance Spectroscopy (ECS) in combination with an MRE antibody or other target-capturing molecule on a working electrode. It will be understood that the methods described herein are generally described with respect to a certain point-of-care apparatus that is generally described in relation to certain embodiments disclosed herein. It will be understood, however that other types of devices can be used to implement the systems and methods described herein.

Generally, some type of bodily fluid, such as tears or serum, is drawn to a working electrode surface that includes a reagent. The reagent includes an antibody that will bind or otherwise recognize a biomarker included in the fluid. Alternatively, the reagent can include an antigen(s) that can bind or recognize an antibody. A current can then be applied to the electrode and the response can be measured at a variety of frequencies. Calibration allows both the optimum frequency to be determined as well as the response for normal levels of whatever biomarker is being detected. Algorithms are then applied to detect elevated, or lowered levels of the biomarker that exceed certain thresholds, such that they indicate a condition or disease as well as what treatment options are appropriate.

Figure 1A:
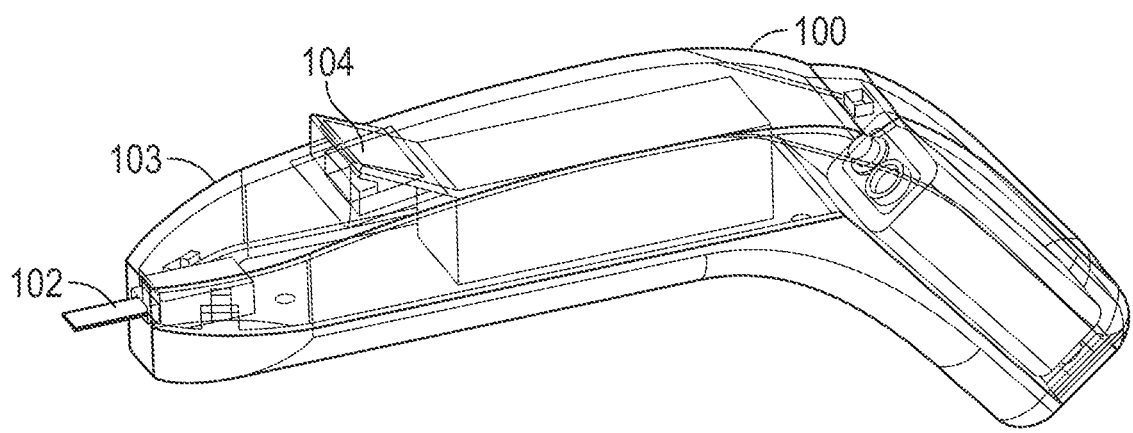
FIGS. 1A-B is a diagram illustrated a device configured in accordance with one embodiment.
Figure 1B:
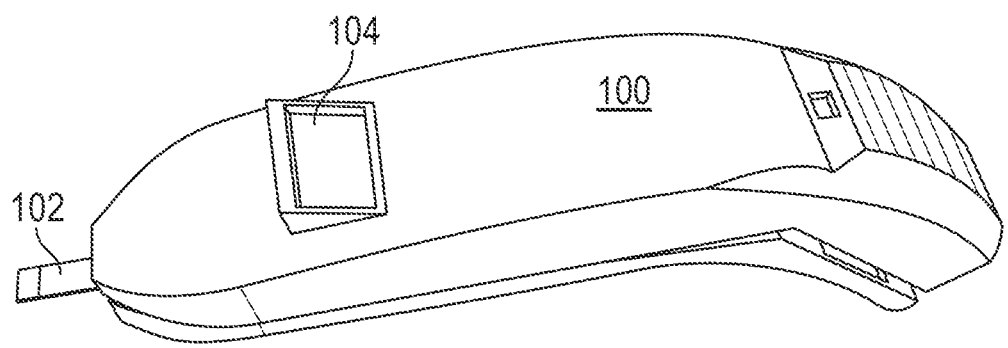

For example, FIGS. 1A-B illustrate the form-factor for a point-of-care device in accordance with one embodiment. The device of FIGS. 1A-B is designed to fit comfortably in the hand like the currently available products such as the Tono-pen or the iPen. As can be seen the device of FIGS. 1A-B features a handheld structure 100 with a disposable test strip/sensor 102 that can be easily inserted at the end 103 of device 100 and then discarded after use. A screen 104 can be included on the top or bottom (top in FIGS. 1A-B) to display, e.g., any measurement results.

Figure 3:
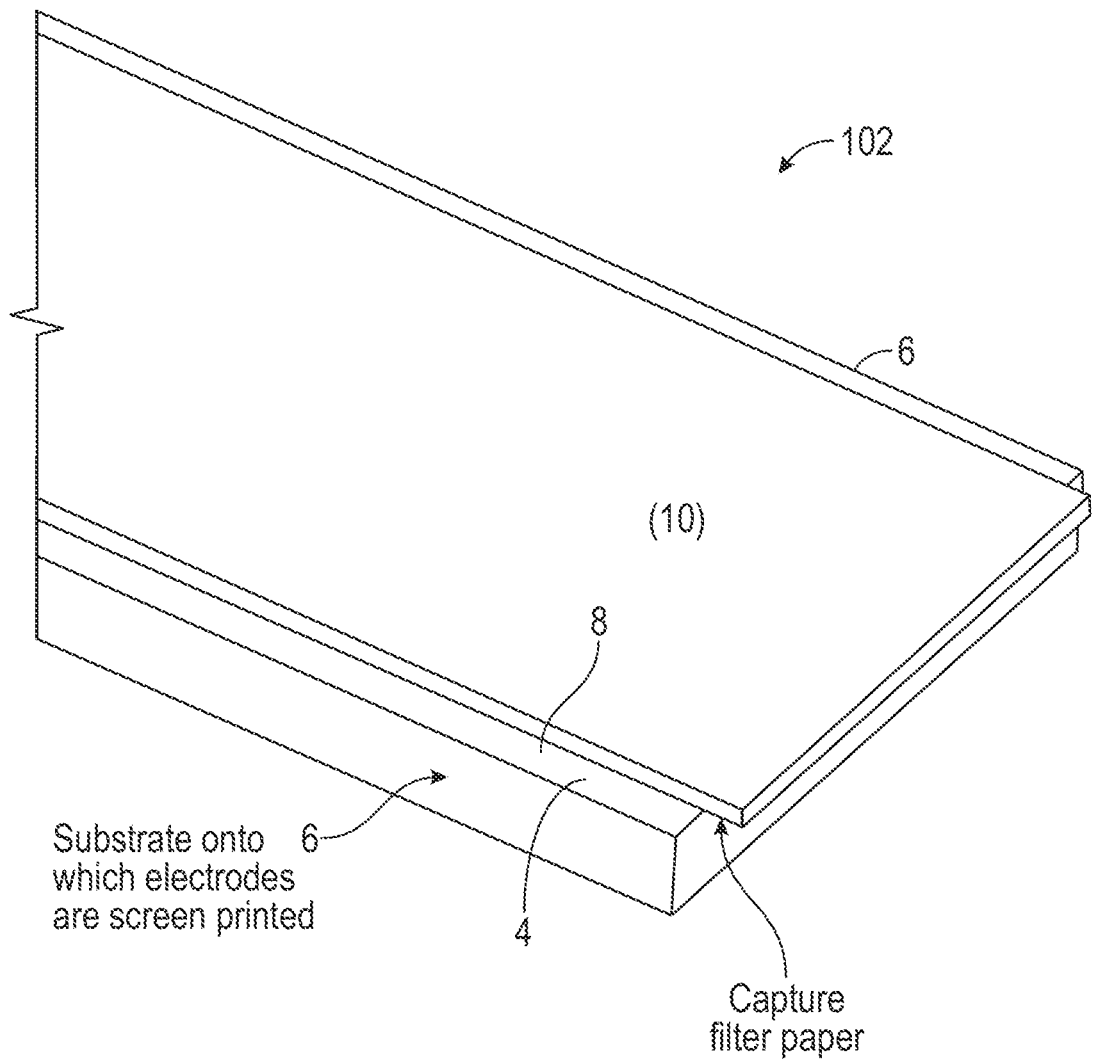
FIG. 3 is a diagram illustrating an example sensor strip that can be used with the device of FIG. 1.

FIG. 3 illustrates an example sensor strip 102 in accordance with one example embodiment. The embodiment illustrated in FIG. 3 can be referred to as a fluid capture test strip embodiment that comprises a PVC, mylar or similar substrate 6 with screen-printed electrode leads (including dried reagents and protein, antibody, other biologic or chemical probes as the target-capturing molecule) 8, and filter paper 10 to absorb tear fluid, with the shape and dimensions of filter paper to be determined based on absorption tests, for example, ~1.75×1.75 mm. The dimensions of a three-lead electrode are determined based on the filter paper dimensions, with the electrode materials including one or more of gold, platinum, titanium, carbon conductive ink, silver chloride ink, and novel mesoporous carbon ink and glue, for example, to facilitate electrochemical measurement through a phase shift of a bound complex of a target-capturing molecule and the molecule of interest. Mesoporous carbon in combination with, for example, an antibody increases the surface area and permits larger amounts of antibody to be loaded onto an electrode thus improving efficiency of detection.

Thus, for example, tear fluid can be drawn to a custom electrode from the eye using filter paper. The presence of biomarkers associated with dry eye or some other disease or condition, such as cancer, can then be detected in the tear fluid using EIS or ECS in a handheld point-of-care device.

For example, as shown in FIG. 3, a sensor strip 102 can be utilized. The sensor 102 may include PVC or similar substrate 4 and screen-printed electrode leads 6, which include dried reagents and one or more target-capturing molecules, e.g., an antibody or other protein (together, 8) for subsequent tear assay. In addition to screen-printed leads, the sensor may utilize other methods of electrode fabrication (laser etching, photolithography, sputtering etc.).

Figure 6:
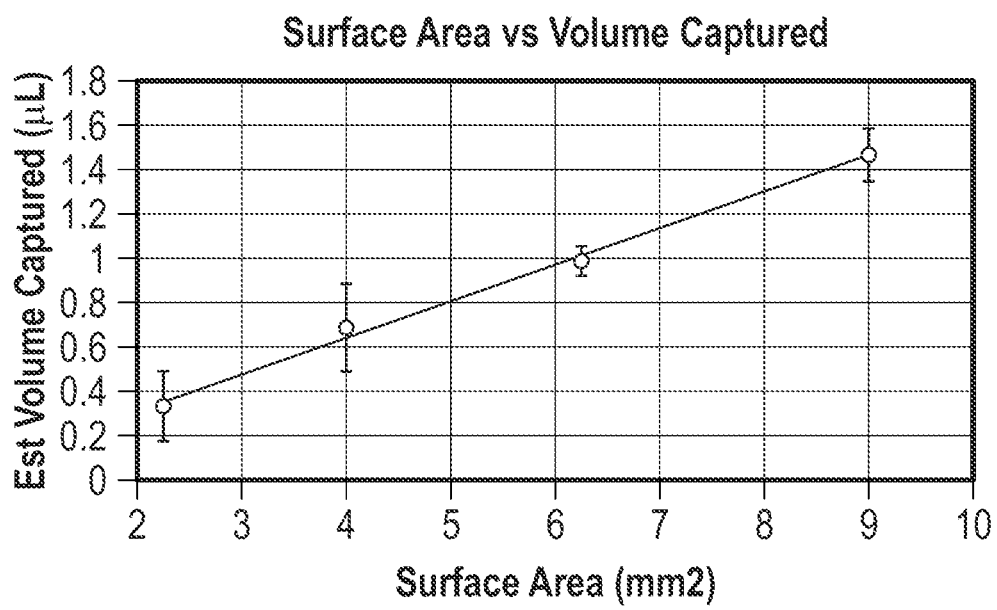
FIG. 6 is a graph and chart illustrating the results of sensor strip saturation test that can be used to optimize the design of the sensor strips of FIGS. 3-5A-D.

Coupled to substrate 4 is an absorbent material, such as filter paper 10, to absorb a bodily fluid including blood, gingival crevicular fluid, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, and suspect tissues or any other constituents of the body which may contain the target molecule of interest with the shape and dimensions of filter paper determined based on absorption tests. For example, the filter paper may be ~1.75 mm×1.75 mm. A determination of actual tear fluid volume captured and reproducibility was performed for four filter paper sizes to determine the amount of tear fluid each size can absorb when exposed to a 64 µL pool of tear fluid. The results are illustrated in FIG. 6.

Figure 2:
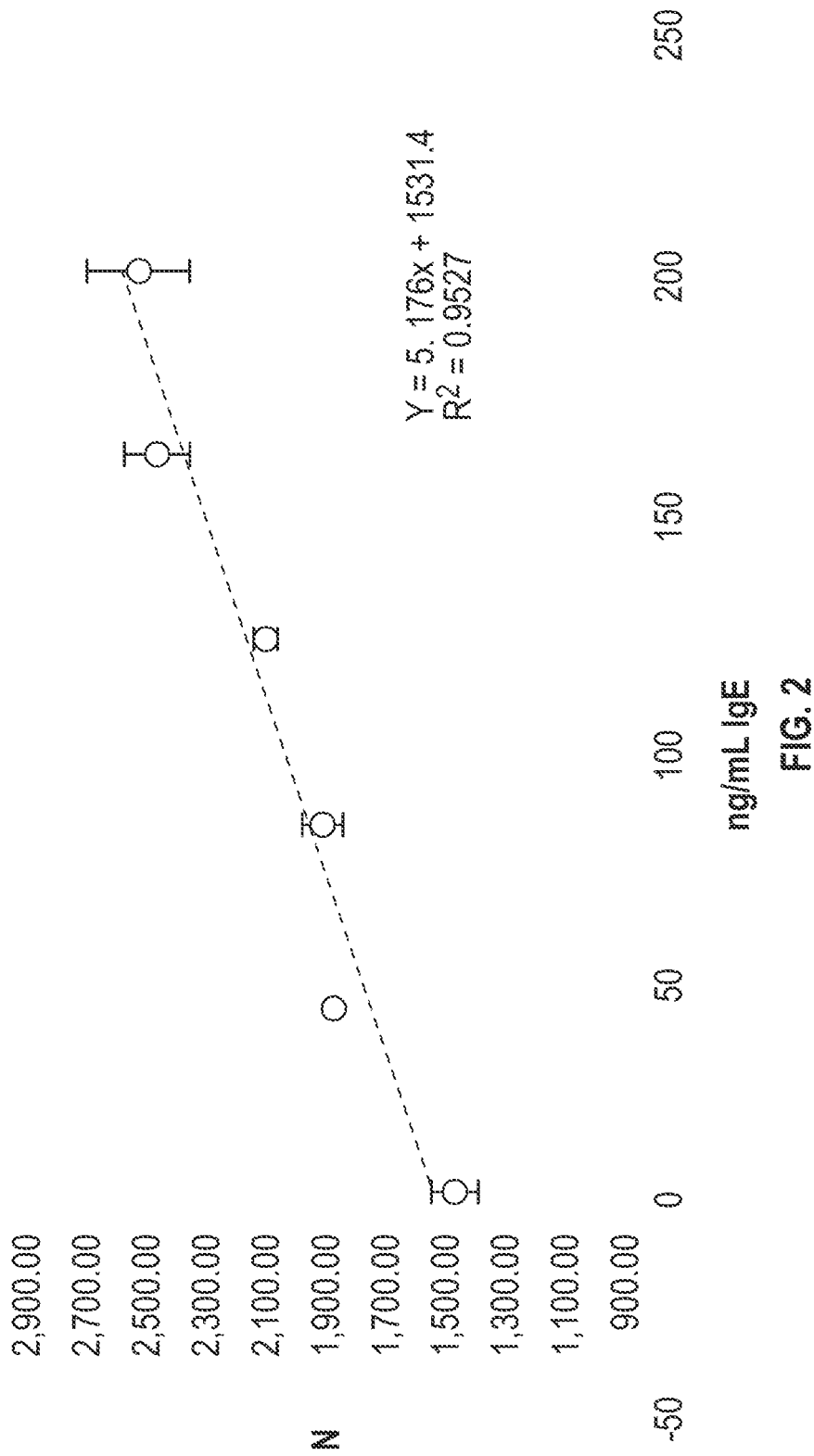
FIG. 2 is a graph illustrating example electrochemical measurements that can be made with the device of FIG. 1A-B.

FIG. 2 illustrates the types of electrochemical measurements that can be made during a calibration process. In this case, complex impedance values are measured then the calibration curve equations (samples shown in the figures described below) are used to convert the measured impedance to a concentration of an analyte at its signature or at a range of optimal frequencies. The calibration curve equations can, for example, be programmed into the handheld device of FIG. 1 to convert measured complex, real or imaginary impedance or phase shift into analyte concentration.

FIGS. 4a-4b illustrate further example embodiments of a sensor strip 102 that can be used, e.g., in conjunction with the device of FIG. 1. The sensor in this embodiment includes 4 layers of screen print inks, each with its own stencil. The complete sensor is shown (right) with a close view of the tip 112, where the filter paper 10 will interface.

FIGS. 5A-D depict another example embodiment of a sensor strip 102 that can be used in conjunction with the device of FIG. 1. The four layers of ink in this embodiment are shown as separate stencil designs as they would be printed, the first layer in this example being carbon, then Ag/AgCl, then mesoporous carbon, with an insulation layer.

Additionally, gold, platinum and/or titanium electrodes can be used as a substrate for immobilization of an MRE.

In summary, sensors have been developed that include one or more target-capturing molecules (for example, antibody immobilized on a working electrode) that have distinct frequency in the bound and unbound states, as well as impedance or capacitance measurements that vary with the amount (concentration) of bound target molecules.

In all sensor embodiments, the sensor would be operably configured to use electrochemical impedance or capacitance as a means to generate a calibration line across a range of analyte concentrations. For example, a power supply computer/software, potentiostat, and/or further EIS or ECS components necessary for the sensor to operate/provide measurements are provided.

Thus, the apparatus described herein provides a platform for developing and implementing various electrochemical impedance and/or electrochemical capacitance sensing protocols, apparatus (such as a handheld device), and systems. Accordingly, imaginary impedance and/or phase shift can also be used to detect and quantify analytes of interest in various biological samples.

Figure 9:
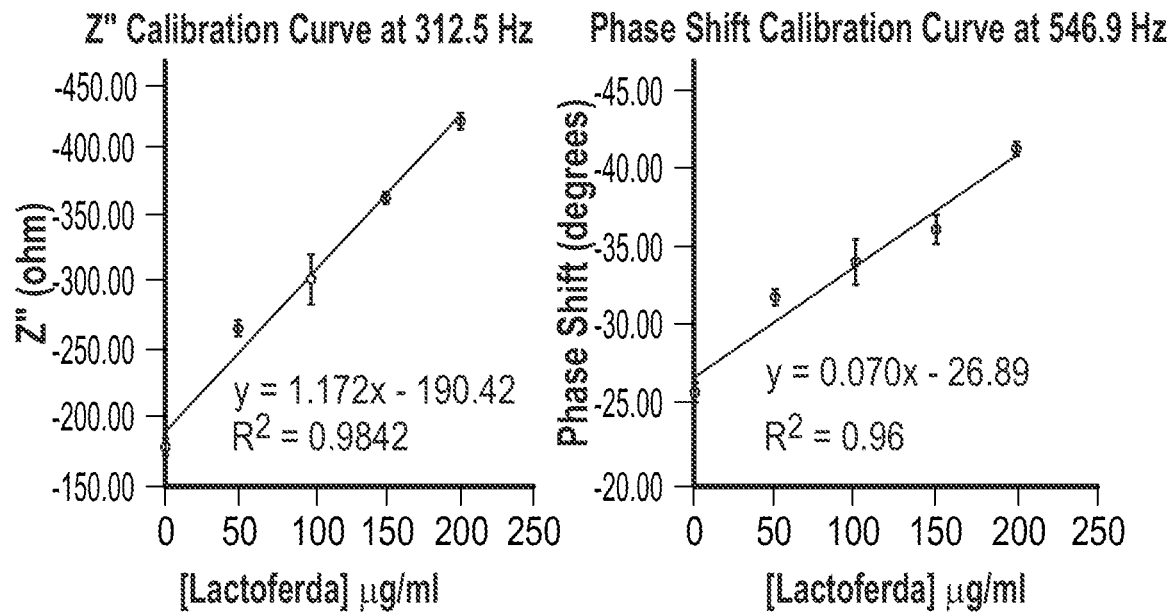
FIG. 9 depicts calibration curves from an imaginary impedance approach (left) and a phase shift approach (right) to analyte detection through EIS.
Figure 10:
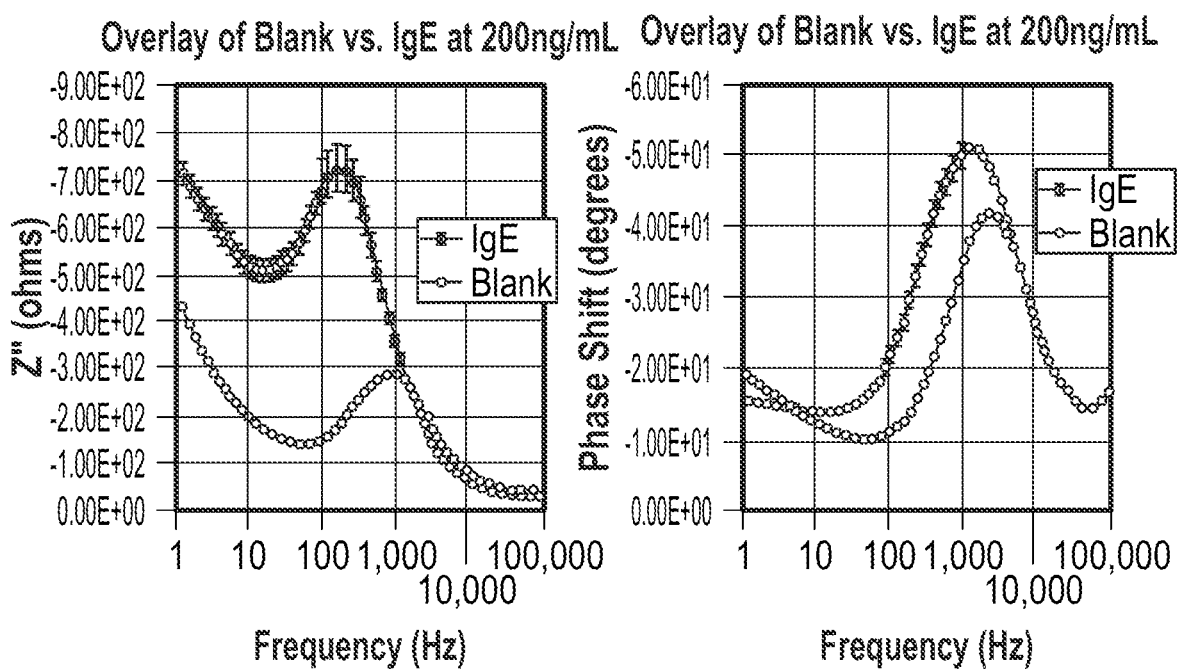
FIG. 10 shows a data overlay of blank versus IgE from an imaginary impedance approach (left) and a phase shift approach (right)

For example, as seen in FIGS. 9 and 10, optimal frequencies differ by analyte and method of detection (phase shift Θ or imaginary impedance Z"). For Lactoferrin, for example, when using imaginary impedance Z", the optimal frequency is 312.5 Hz. When using phase shift Θ, the optimal frequency becomes 546.9 Hz. From these experiments, concentration was found to be linear over therapeutic range (0.5-2 mg/mL) for lactoferrin, while the limit of detection was found to be <20 ng/mL on sensor for IgE.

Optimal frequency or range of frequencies that is "most robust" against changing variables yet still very specific to target binding have been identified for various targets. The identification of the optimal frequencies can improve reproducibility. Thus, for example, FIGS. 12-17 illustrates various measurement curves associate with a calibration process that identifies the optimal frequency or frequency range.

FIG. 12 depicts EIS data (left) after scanning from 100,000 Hz to 1 Hz at a formal potential of 0.1V and an AC potential of 5 mV over a range of lactoferrin concentrations (0-200 µg/mL). The optimal frequency to prepare a quantitative calibration line was found to be around 312 Hz. A plot of $R^2$ and slope against frequency (right) can be used to pick a single frequency or range of frequencies at which to generate a calibration line.

FIG. 13 shows a comparison of original (left) and background subtracted (right) lactoferrin calibration lines at 312 Hz and 21.2 Hz in the form of y=mx+c with $R^2$ values of 0.9842 and 0.9885 respectively.

FIG. 14 shows a plot of background subtracted $R^2$ and slope against frequency (left) and background subtracted EIS scans from 100,000 Hz to 1 Hz (right) at a formal potential of 0.1V and an AC potential of 5 mV over a range of lactoferrin concentrations (50-200 µg/mL).

Figure 15:
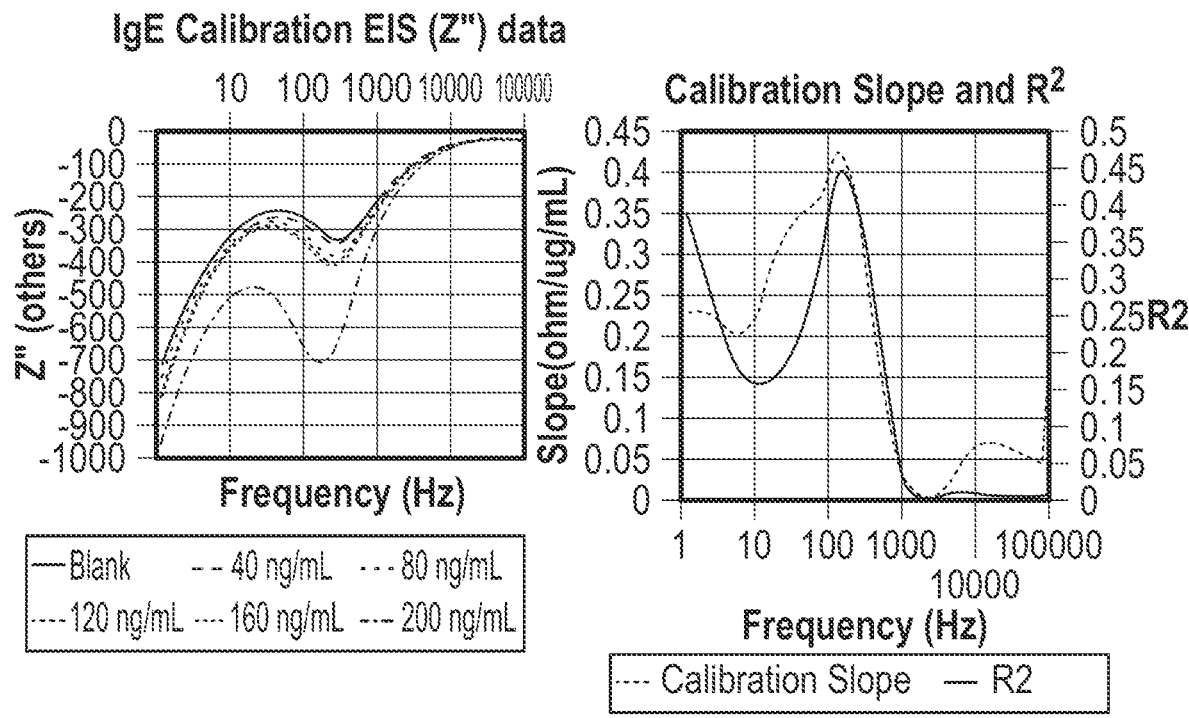
FIG. 15 depicts EIS data (left) after scanning from 100,000 Hz to 1 Hz at a formal potential of 0.1V and an AC potential of 5 mV at a range of IgE concentrations (0-200 ng/mL). Optimal frequency to prepare a quantitative calibration line was found to be around 147 Hz. A plot of $R^2$ and slope against frequency (right) can be used to pick a single frequency or range of frequencies at which to generate a calibration line.

FIG. 15 depicts EIS data (left) after scanning from 100,000 Hz to 1 Hz at a formal potential of 0.1V and an AC potential of 5 mV at a range of IgE concentrations (0-200 ng/mL). Optimal frequency to prepare a quantitative calibration line was found to be around 147 Hz. A plot of $R^2$ and slope against frequency (right) can be used to pick a single frequency or range of frequencies at which to generate a calibration line.

Figure 16:
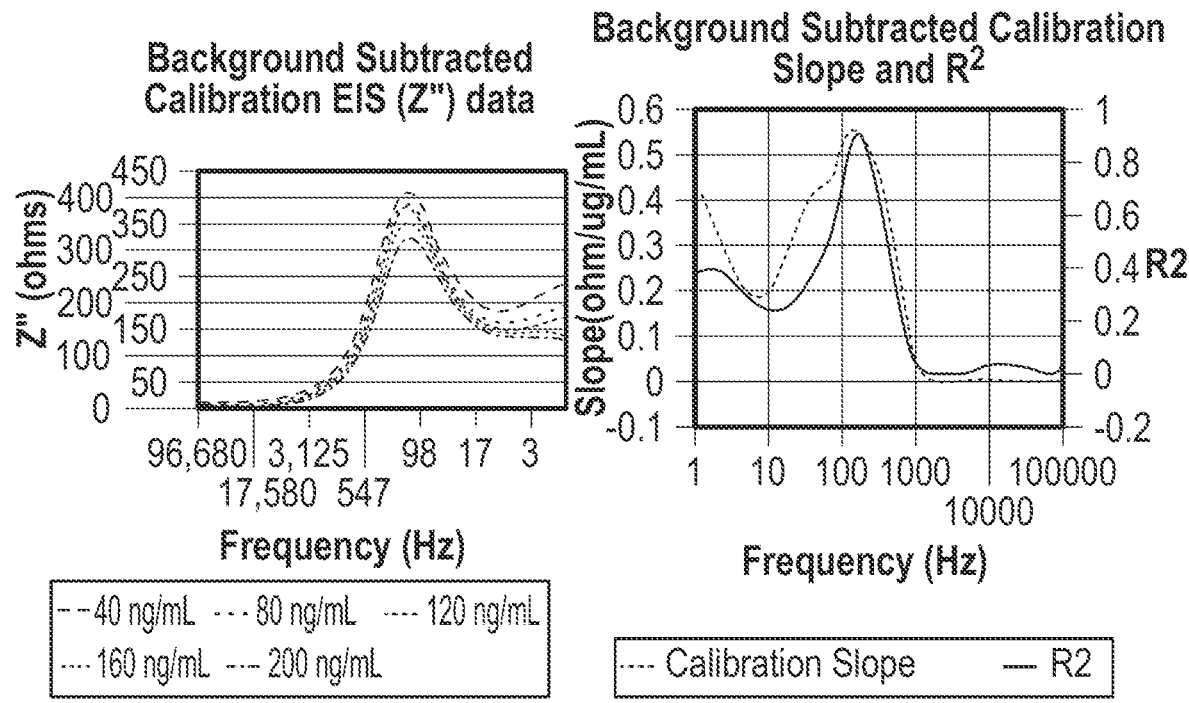
FIG. 16 shows a plot of background subtracted $R^2$ and slope against frequency (left) and background subtracted EIS scans from 100,000 Hz to 1 Hz (right) at a formal potential of 0.1V and an AC potential of 5 mV over a range of IgE concentrations (50-200 ng/mL)

FIG. 16 shows a plot of background subtracted $R^2$ and slope against frequency (left) and background subtracted EIS scans from 100,000 Hz to 1 Hz (right) at a formal potential of 0.1V and an AC potential of 5 mV over a range of IgE concentrations (50-200 ng/mL)

Figure 17:
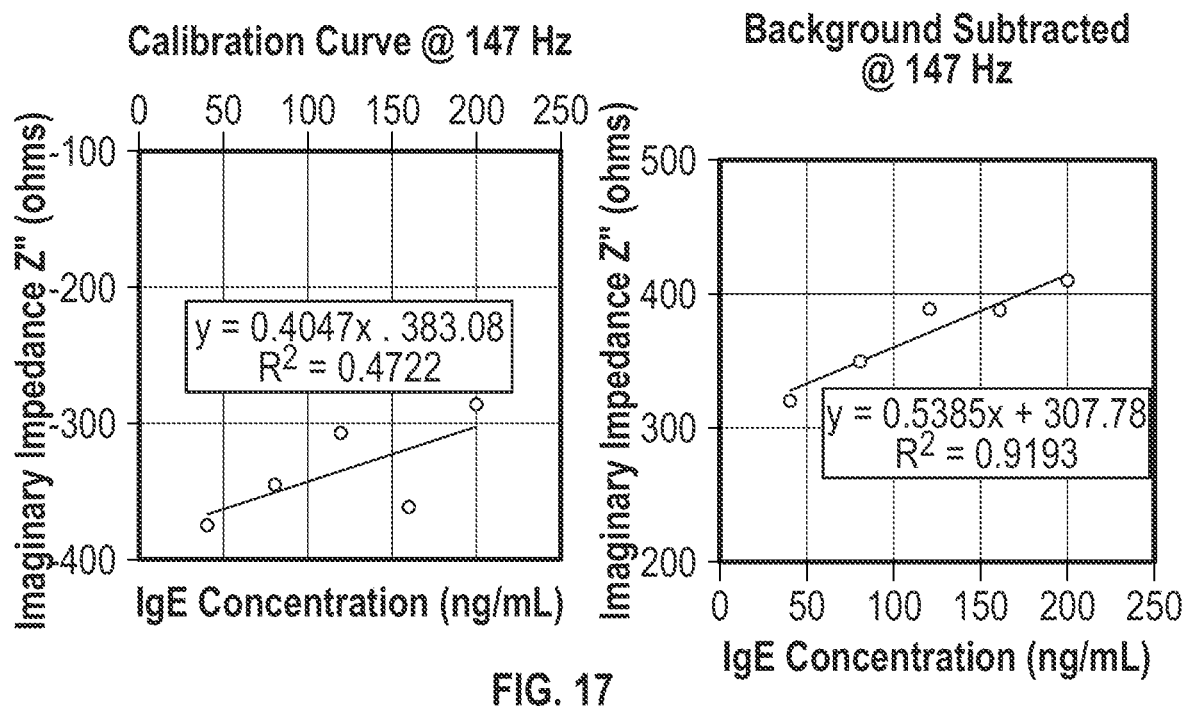
FIG. 17 shows a comparison of original and background subtracted IgE calibration lines. Optimal frequency was found to be 147 Hz.

FIG. 17 shows a comparison of original and background subtracted IgE calibration lines. Optimal frequency was found to be 147 Hz.

Figure 19:
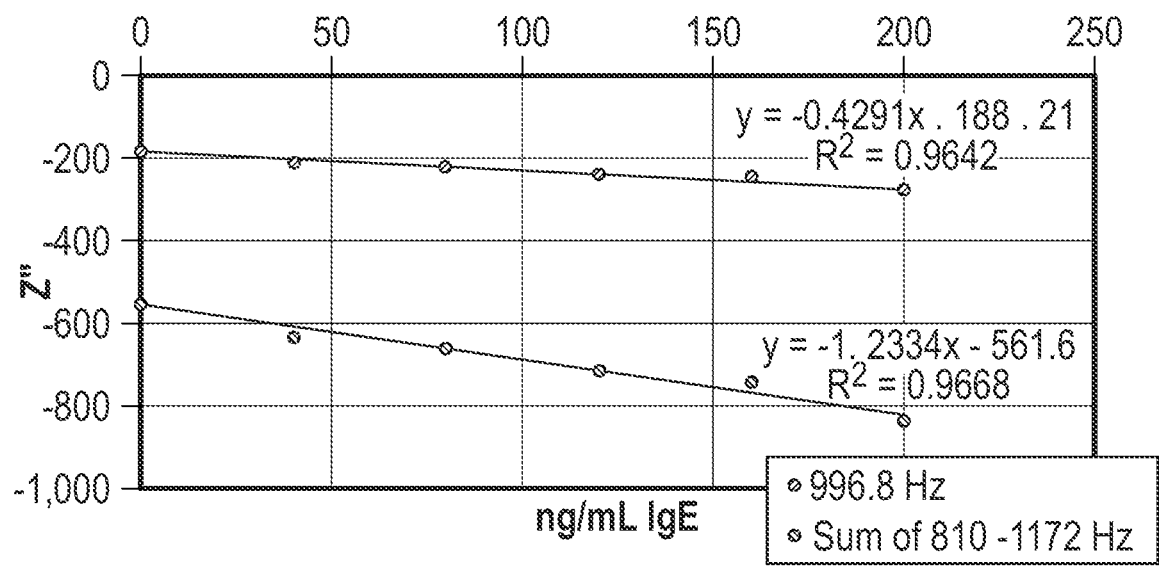
FIG. 19 shows a comparison of a calibration line at a frequency of 996.8 Hz compared with a calibration line summed over the frequency range 810-1172 Hz.

When electrochemical impedance spectroscopy is performed on a sample over 1-100,000 Hz, a dataset featuring measurements of real impedance, imaginary impedance, complex impedance and phase angle is generated for each frequency or range of frequencies studied. A dataset of either real impedance, imaginary impedance, complex impedance or phase angle can either be used to generate a calibration line at a single frequency (FIG. 19, dotted line) or summed to generate a calibration line over a range of frequencies (FIG. 19, solid line).

When a sensor is made, it has a baseline impedance signal (either phase shift or imaginary impedance), which can vary among batches depending on the variance in fabrication process. Once the blank is subtracted, the remaining signal can be considered as a "normalized" signal. The normalized impedance signal across the frequency spectrum can be compared across batches and a best, resonating frequency can be identified at which the response is always very reproducible at this specific frequency. The response should also correlate to the analyte concentrations.

For example, FIG. 7 is a graph illustrating a subset of data from an imaginary impedance approach to analyte detection through EIS after scanning from 100,000 Hz to 1 Hz at a formal potential of 0.1V and an AC potential of 5 mV for both a lactoferrin sensor and the blank sensor. FIG. 8 is a graph of a subset of data from a phase shift approach to analyte (lactoferrin) detection through EIS for both as well.

Figure 18:
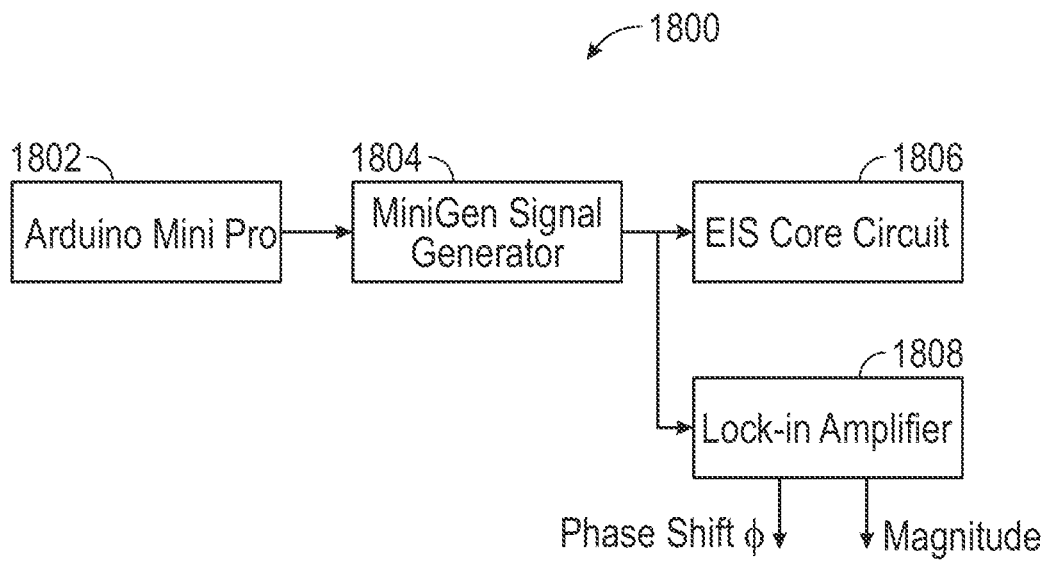
FIG. 18 is a diagram illustrating an example block diagram of a circuit that can be used in conjunction with the sensors of FIGS. 3-5 and included in the device of FIG. 1A-B.

In terms of a reader for impedance or capacitance measurements, FIGS. 11 and 18 show a hardware circuit block diagram and a layout and design of a radio frequency "reader" for measurement of a target capturing molecule/target complex that uses EIS to generate a low radio frequency voltage at a specific frequency.

As illustrate in the block diagram of FIG. 18, in one embodiment, an electrochemical impedance spectroscopy (EIS) system 1800 can be designed using electrically discrete components.

For example, the system 1800 can comprises a sinewave signal generator comprising an Arduino Mini Pro board 1802 and MiniGen Signal Generator board 1804, which generally have the same form factor in size and they overlap on each other due to compatible pin configuration, which further reduces the size of electronics. An Arduino Mini Pro board 1802 can be programmed to communicate with MiniGen Signal Generator board 1804 to generate a sine wave signal that is then applied to the EIS core circuit 1806. The EIS core circuit 1806 converts down this sine wave signal to appropriate amplitude and formal potential, which serves as an input excitation signal to the cell (or the sensor part). Once the sensor returns the signal (aka the output current), it is converted in the same EIS core circuit 1806. The returned signal (output signal) is then compared to the input signal via lock-in amplifier 1808 and the phase shift and magnitude of the signal are then converted to analyte concentration by a predetermined algorithm. The results can then be displayed on a screen that is operably connected to the other reader components.

FIG. 11 is a circuit diagram illustrating the reader 1800 in a little more detail. As can be seen signal generator 1810 provides a signal to the input of amplifier 1812, the output of which is feedback to the other input and to one of the sensor 2 electrodes 4. The other electrode 4 is coupled with the input of amplifier 1814. The circuit of FIG. 11 allows a comparison of the phase and amplitude difference between the input and the output, i.e., the change introduced by the electrochemical effect introduced by the sensor and any analyte detected thereby.

Thus for example, to collect tear film, only the filter paper attached to a test strip briefly contacts the edge of the eye proximal to the lower lacrimal lake to obtain ≤0.5 μL of tear fluid. The device, e.g., of FIG. 1 is designed to facilitate tear collection in a quick and ergonomic fashion. The device can then make a sound when enough tear fluid is captured thus signaling that the handheld can be removed from the eye region.

Next, tear fluid can be analyzed. The tear fluid on the filter paper wets the electrodes, which perform electrochemical impedance or electrochemical capacitance measurements. These electrochemical measurements are converted to an analyte concentration based on pre-programmed calibration curves. For example, if the output signal is Y, then using Y=mx+c, where m and c are known constants and x is the concentration being solved. Then once Y is measured, x can be calculated easily. Next, the concentration can be displayed on a reader for the ocular analyte of interest, which may include, but are not limited to, IgE, Lactoferrin, osmolality measurements, MMP9, adenovirus, glucose and/or any molecule to which an antibody exists and which can be immobilized onto the working electrode of an electrochemical sensor.

Figure 20:
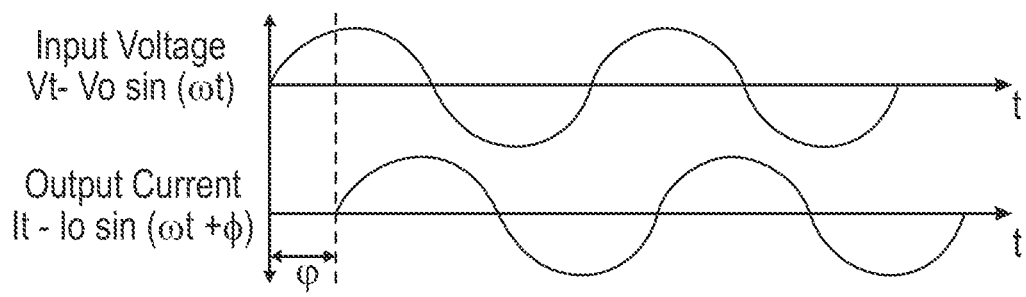
FIG. 20 is a diagram illustrating the input versus the output of the circuits of FIGS. 11 and 18.

By way of additional example, to measure the electrochemical impedance of an electrochemical cell, an AC potential is applied as an input as illustrated in FIG. 20 and the current passing through the cell is measured. If an electrochemical cell exhibits purely resistive impedance then there is no phase shift between input voltage signal and current passing through the cell assuming the input AC potential is sinusoidal in nature. Also, the frequency of both current and voltage waveform will be same. If an electrochemical cell exhibits purely capacitive impedance, then the current waveform will lead the voltage waveform by 90 degrees. If an electrochemical cell exhibits purely inductive impedance, then the current will lag the voltage by 90 degrees. In the real world, an electrochemical cell with solution exhibits a combination of resistive, capacitive and inductive impedance.

Given an input excitation signal in time domain with the form:

$$V_t = V_0 \sin(\omega t)$$

Radial frequency $\omega$ can be expressed in terms of frequency f in Hertz as $\omega = 2\pi f$. The response signal is shifted in phase by $\varphi$ degrees and is given by, $$I_t = I_0 \sin(\omega t + \phi)$$

Where, $I_0$: Amplitude of response current $\Phi$: Phase shift in current response.

A complex impedance is given by dividing instantaneous voltage signal with instantaneous response current.

$$Z = \frac{V_t}{I_t}$$

$$Z = \frac{V_0 \sin(\omega t)}{I_0 \sin(\omega t + \phi)}$$

$$Z = \frac{Z_0 \sin(\omega t)}{\sin(\omega t + \phi)}$$

Such complex impedance is represented in terms of phase shift $\varphi$ and magnitude $Z_0$. The same impedance can be represented using Euler's relationship as follows:

$$Z(\omega) = Z_0(e^{j\phi})$$

$$Z(\omega) = Z_0(\cos \phi + j \sin \phi)$$

From the above expression, impedance can be plotted over the spectrum $\omega$ rad/sec (or in frequency Hz) by only measuring two components: magnitude $Z_0$ and phase shift $\varphi$.

The results from device or system measurements may be displayed on the reader device and/or an external device such as a phone or computer, and diagnosis of dry eye syndrome, other ocular diseases and biomarkers of cancer thereby is made conveniently.

In another example, 60 μg/mL Lactoferrin antibody solution can be applied to electrode and dried. The electrode can then be subjected to gluteraldehyde vapor for 1 hour and the cross-linking reaction is stopped. Lactoferrin antigen is added to 50% of the sensors and incubated at 4° C. for 15 hours. Next, EIS measurements are run from a frequency range of 1-100,000 Hz.

In another example, the systems and methods described herein can be used to detect the presence of cancer and in particular breast cancer. For example, U.S. Patent Publication Nos. 2014/0154711 and 2016/003786, which are incorporated herein by reference as if set forth in full, describe various biomarkers that can be detected in tears or other bodily fluids and that act as indicators of cancer. For example, Table 2A of the '786 Publication lists biomarkers with an increased expression in cancer, while table 2B lists biomarkers with a decreased expression. Thus, after proper calibration and optimization as described herein, the sensor strip of FIG. 3 can include the proper reagents to allow detection by, e.g., the device of FIG. 1, of the elevated or decreased presence of the biomarkers included in tables 2A and 2B, which are recreated below.

The '711 Publication also lists α-Defensin 1, α-Defensin 2, and α-Defensin 3 as biomarkers that can indicate the presence of cancer.

Figure 21:
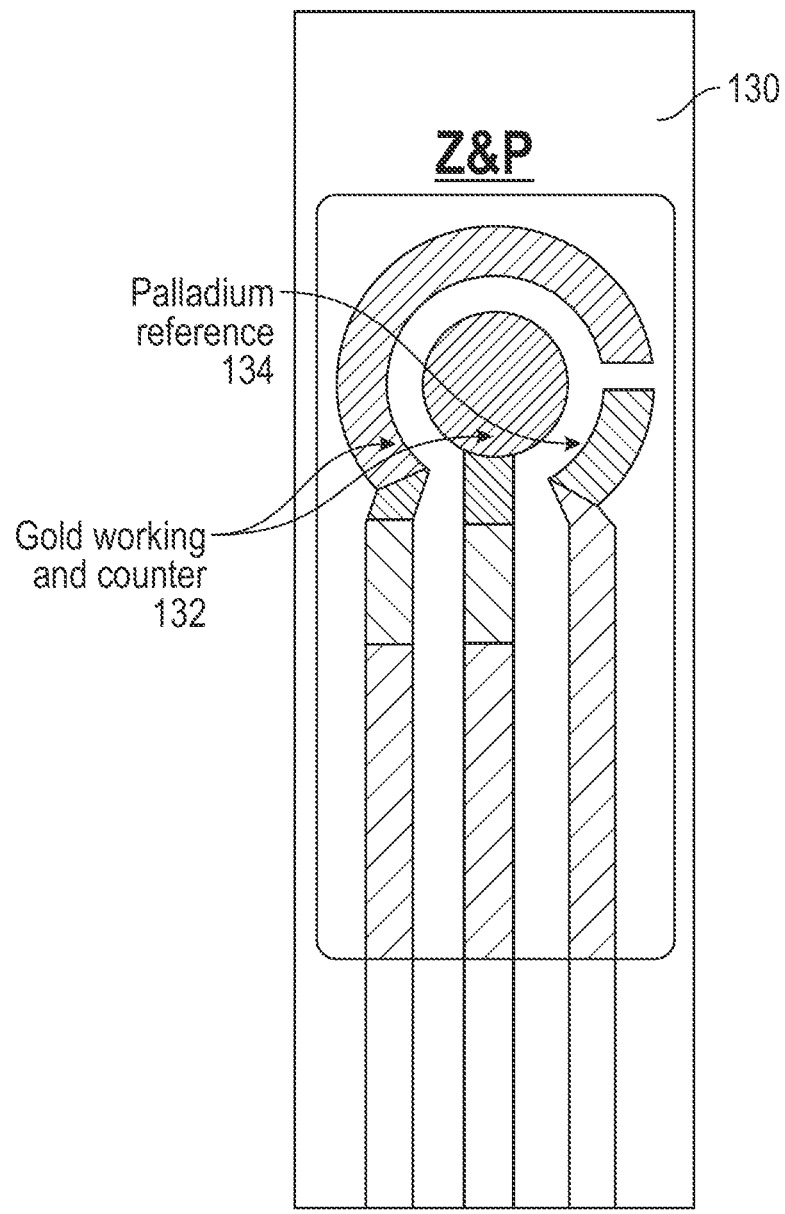
FIG. 21 is a diagram illustrating an example embodiment of a sensor electrode that is constructed from gold.
Figure 22:
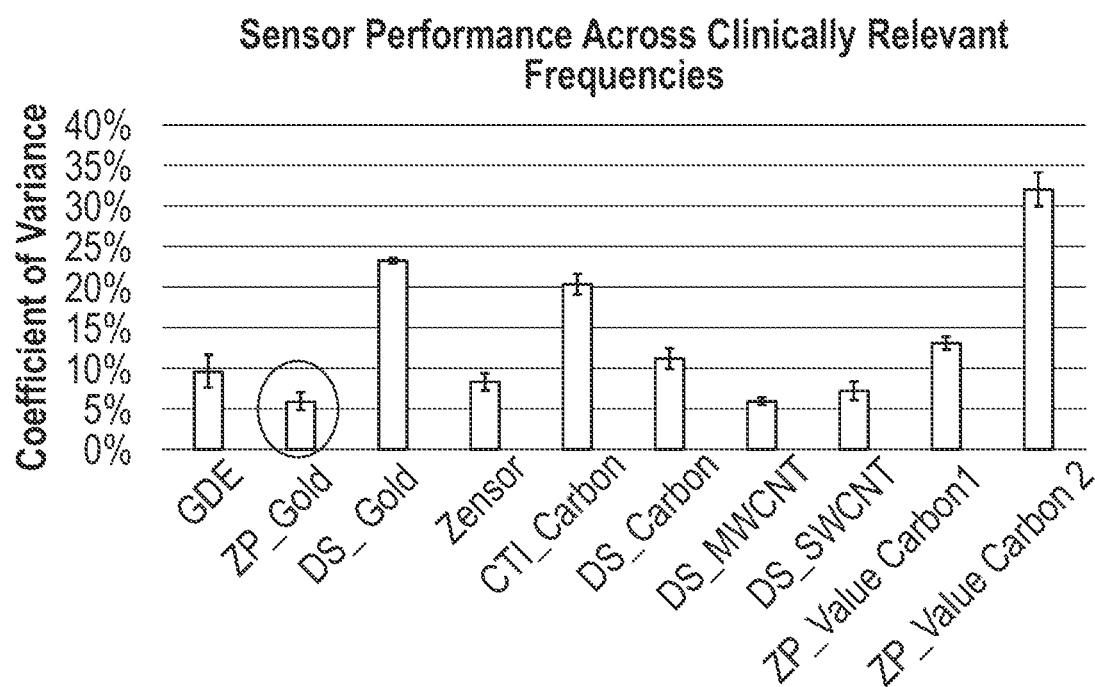
FIG. 22 shows the relative sensitivity or variance of various electrode material.

In another example, the systems and methods described herein can be used to detect the presence of cancer and in particular breast cancer/metastatic breast cancer by measurement of soluble HER-2 protein. For example, FIG. 21 is a diagram illustrating the design of an electrode 130 that includes a gold working and counter region 132 as well as a palladium reference 134. FIG. 22 illustrates than when fabricated appropriately and when combined with adequate calibration and detection algorithms, the gold sensor 130 of FIG. 21 can result in relatively low variance in terms of performance, which makes gold well suited to the detection of HER-2.

It should be noted that the systems and methods described herein can be used for label-free or labeled detection. In certain embodiments, labeled detection can make it easier to detect the target analyte using the, e.g., EIS detection systems and methods described.

TABLE 2A

Biomarkers with an increase expression in cancer as compared to control samples.

| Protein ID | P-Value | Fold Change |
| --- | --- | --- |
| CLEC3B | 0.067 | No expression in control |
| KLK8 | 0.07 | No expression in control |
| C8A | 0.149 | No expression in control |
| HRC | 0.17 | No expression in control |
| KLK13 | 0.178 | No expression in control |
| C7 | 0.207 | No expression in control |
| ALDH1A1 | 0.24 | No expression in control |
| APOL1 | 0.32 | No expression in control |
| MUC-1 | 0.27 | 40.6 |
| BLMH | 0.212 | 38.1 |
| SPRR1B | 0.117 | 35.1 |

TABLE 2A-continued

Biomarkers with an increase expression in cancer as compared to control samples.

| Protein ID | P-Value | Fold Change |
|---|---|---|
| SERPINB2 | 0.11 | 16.1 |
| Putative uncharacterized protein | 0.165 | 11.7 |
| RAB-30 | 0.153 | 11.3 |
| C4A | 0.099 | 9.6 |
| PRDX6 | 0.14 | 7.6 |
| CFHR1 | 0.169 | 7.4 |
| A1BG | 0.11 | 7.2 |
| GGH | 0.14 | 7.1 |
| EZR | 0.066 | 6.3 |
| SERPINF2 | 0.16 | 5.9 |
| HPX | 0.1 | 5.5 |
| CRISP3 | 0.0238 | 5.2 |
| CPA4 | 0.14 | 4.8 |
| PGLYRP2 | 0.06 | 3.9 |
| CASP14 | 0.068 | 3.3 |
| Ig Kappa Chain V-III region POM | 0.001 | 2.6 |
| ALB | 0.014 | 2.4 |
| CFH | 0.042 | 2.1 |
| SLC34A2 | 0.105 | 29.3 |

TABLE 2B

Biomarkers with a decrease expression in cancer samples as compared to controls

| Protein ID | P-value | Fold Change |
|---|---|---|
| GAS6 | 0.045 | 3.5 |
| CTSL1 | 0.051 | 3.4 |
| SFRPI | 0.059 | 3.4 |
| BPI | 0.045 | 2.5 |
| CHID1 | 0.0546 | 2.2 |
| MSN | 0.0545 | 2.06 |
| ERAP1 | 0.014 | 1.6 |
| QPCT | 0.045 | 1.6 |
| ATRN | 0.062 | 1.6 |
| LTF | 0.051 | 1.5 |

What is claimed is:

1. An apparatus for detecting one or more analytes in a bodily fluid sample utilizing Electrochemical Impedance Spectroscopy (EIS) or Electrochemical Capacitance Spectroscopy (EC S), comprising:
   an electrochemical sensor comprising:
      a substrate;
      a plurality of electrodes including a working electrode disposed on the substrate,
      a filter paper interfaced with the plurality of electrodes, the filter paper (i) disposed on the plurality of electrodes and (ii) arranged to collect the bodily fluid and wet the plurality of electrodes with the bodily fluid, and
      a plurality of target-capturing molecules immobilized to the working electrode,
   wherein an electrochemical impedance or electrochemical capacitance measurement of one or more analytes in the bodily fluid is measured based on a current applied to the plurality of electrodes when the one or more analytes bind to the plurality of target-capturing molecules of the plurality of target-capturing molecules.

2. The apparatus of claim 1, wherein said working electrode comprises one or more of a carbon conductive ink, a silver/silver chloride ink, and a mesoporous carbon ink.

3. The apparatus of claim 1, wherein said target-capturing molecule is an antibody.

4. The apparatus of claim 3, wherein said antibody is coupled to said sensor in dry form.

5. The apparatus of claim 1, wherein the target-capturing molecule binds to the one or more analytes that is one of HER-2, α-Defensin 1, α-Defensin 2, α-Defensin 3, CLEC3B, KLK8, C8A, HRC, KLK13, C7, ALDH1A1, APOL1, MUC-1, BLMH, SPRR1B, SERPINB2, putative uncharacterized protein, RAB-30, C4A, PRDX6, CFHR1, A1BG, GGH, EZR, SERPINF2, HPX, CRISP3, CPA4, PGLYRP2, CASP14, 1 g Kappa Chain V-III region POM, ALB, CFH, SCL34A2, GAS6, CTSL1, SFRP1, BP1, CHID1, MSN, ERAP1, OPCT, ATRN, and LTF.

6. The apparatus of claim 1, wherein the electrochemical sensor further comprises an insulating layer disposed over first portions of each of the plurality of electrodes and wherein second portions of each of the plurality of electrodes are uncovered by the insulating layer, wherein the filter paper is disposed over the second portions.

7. The apparatus of claim 6, wherein the filter paper overlaps with part of the insulating layer, and wherein the filter paper and the insulating layer together expose third portions of each of the plurality of electrodes.

8. The apparatus of claim 7, wherein the substrate is an elongated strip having a first end and a second end, wherein the second portions of each of the plurality of electrodes are disposed on the first end and the third portions of the plurality of electrodes are disposed on the second end.

9. The apparatus of claim 1, further comprising a handheld structure with an opening, wherein the electrochemical sensor, including a part of each of the plurality of electrodes, is positioned partially inside the opening.

\* \* \* \* \*